United States Patent [19]

Chang

[11] Patent Number: 5,258,490
[45] Date of Patent: Nov. 2, 1993

[54] NON-IRRITATING SOFT GAS PERMEABLE CONTACT LENS AND PROCESS FOR PRODUCING SAME

[76] Inventor: Sing-Hsiung Chang, 61 Buckskin, Danbury, Conn. 06810

[21] Appl. No.: 899,831

[22] Filed: Jun. 16, 1992

Related U.S. Application Data

[63] Continuation of Ser. No. 545,205, Jun. 28, 1990, which is a continuation-in-part of Ser. No. 407,263, Sep. 14, 1989, abandoned, which is a continuation-in-part of Ser. No. 132,174, Dec. 14, 1987, abandoned.

[51] Int. Cl.$^5$ .......................... C08F 6/10; C08F 30/08; C08J 3/00
[52] U.S. Cl. ..................................... 528/488; 528/489; 528/491; 528/492; 528/493; 528/495; 528/496; 523/103; 523/106; 525/327.3; 525/937; 526/279
[58] Field of Search ............... 528/488, 489, 491, 492, 528/493, 495, 496; 523/103, 106, 107; 526/279; 525/326.5, 327.3, 937; 264/1.1

[56] References Cited

U.S. PATENT DOCUMENTS

| | | | |
|---|---|---|---|
| Re. 33,477 | 12/1990 | Loshaek | 526/316 |
| 4,067,839 | 1/1978 | Schultz | 526/916 |
| 4,330,383 | 5/1982 | Ellis et al. | 526/279 |
| 4,492,776 | 1/1985 | Atkinson et al. | 526/261 |
| 4,731,079 | 3/1988 | Stoy | 623/6 |
| 4,829,137 | 5/1989 | Stoyan | 526/246 |
| 4,929,717 | 5/1990 | Chmelir | 528/490 |
| 4,954,586 | 9/1990 | Toyoshima et al. | 526/245 |
| 4,977,229 | 12/1990 | Culberson et al. | 526/279 |
| 5,002,979 | 3/1991 | Stoyan | 526/245 |
| 5,023,305 | 6/1991 | Onozuka et al. | 526/245 |

*Primary Examiner*—Herbert J. Lilling

[57] ABSTRACT

A clinically-acceptable hydrophilic silicone-based soft gas permeable contact lens produced by subjecting the lens material to extraction with a hydrophilic, polar group-containing, organic solvent followed by replacement of the organic solvent with a physiological saline solution.

3 Claims, No Drawings

NON-IRRITATING SOFT GAS PERMEABLE CONTACT LENS AND PROCESS FOR PRODUCING SAME

This is a continuation of copending application(s) Ser. No. 07/545,205 filed on Jun. 28, 1990 which in turn is a continuation-in-part of prior applications Ser. No. 407,263, filed Sept. 14, 1989, abandoned and application Ser. No. 132,174, filed Dec. 14, 1987, abandoned.

BACKGROUND OF THE INVENTION

The present invention relates to contact lenses, and more particularly, to clinically-acceptable silicone-based soft gas permeable contact lenses and methods for their manufacture.

The development and use of plastic materials and compositions for contact lenses has been the subject of much attention over the years.

Among the first such developments was the so-called hard lens utilizing the hard plastic polymethylmethacrylate (PMMA). However, this material does not exhibit a significant degree of oxygen permeability and has very poor surface wettability characteristics. The art then progressed to softer lenses based upon poly 2-hydroxethylmethacrylate (poly HEMA), a material having significantly better oxygen permeability and surface quality than the hard PMMA plastic. Nevertheless, these characteristics were still not as high as desirable or necessary, and lenses of this type often resulted in serious problems of corneal staining, swelling, ulcers, thickness and infection.

Somewhat more recently, based upon better understanding of the corneal requirement of substantial oxygen permeability, the art proposed the use of so-called hard gas permeable (HGP) lenses composed of either of two types of plastic materials, acrylic silicone or acrylic fluorosilicone. See, e.g., U.S. Pat. No. 3,808,178. Generally, the oxygen permeability of HGP lenses can progressively be increased with increasing amounts of the silicone and/or fluorosilicone in the composition; at the same time, however, the surface wettability of the lens becomes progressively poorer. In order to overcome this problem, it is known to incorporate a relatively large amount of methacrylic acid, an ionic material, into the formulation, resulting in the lens surface being negatively charged. While this expedient does lead to improved surface wettability, the negatively-charged surface has a very high absorptivity leading to serious deposition problems. As a consequence, the HGP lens is of only limited potential.

Most recently, hydrophilic soft gas permeable (SGP) lenses have been developed based upon compositions containing, e.g., a polymerizable vinylic siloxane and a hydrophilic vinylic monomer. See, e.g., U.S. Pat. Nos. 4,136,250; 4,139,513; 4,182,822; 4,261,875; 4,343,927; 4,426,389; 4,486,577; 4,605,712; 4,711,943; and 4,837,289. The SGP lenses of this type have excellent oxygen permeability and hydrophilicity. Surprisingly, however, although the lens is highly hydrophilic, its functional (i.e., on the eye) wettability is still relatively poor, and the lens is highly irritable and uncomfortable, often resulting in serious deposition problems, making it highly unsuitable for extended wear.

In the manufacture of early-generation soft contact lenses, the lenses were subjected to an aqueous or physiological saline solution extraction to render them clinically acceptable. See, e.g., U.S. Pat. No. 4,158,089 (Col. 6, line 25) and U.S. Pat. No. 3,937,680 (Col. 6, line 51). The more recently-developed SGP lenses are also subjected to this conventional treatment, i.e., extraction with physiological saline solution. See, e.g., U.S. Pat. No. 4,139,513 (Col. 9, line 16); U.S. Pat. No. 4,261,875 (Col. 5, line 43) and U.S. Pat. No. 4,711,943 (Col. 37, line 32), involving immersion of the lens in a 50/50 v/v methanol/water mixture. The present invention is predicated on the discovery that this form of treatment does not effectively dissolve and extract the residual siloxane monomers and/or their low molecular weight derivatives formed during polymerization. Thus, silicone-based SGP lenses of the prior art contain a substantial amount of residual siloxane monomer and derivatives, resulting in a high degree of irritability, poor wettability and serious deposition problems.

It should be mentioned that the non-polar solvent hexane has been taught in the pre-treatment of a silicone rubber lens, as illustrated in U.S. Pat. No. 3,350,216. However, it has been found that hexane is not suitable for use in the extraction of silicone-based SGP lenses.

It is the primary object of the present invention to provide silicone-based SGP lenses, and processes for their production, which have enhanced clinical acceptability by reason of greatly reduced levels of residual monomers or other reactants and/or low molecular weight by-products of the polymerization reaction used to produce the lens material.

SUMMARY OF THE INVENTION

This and other objects are achieved by the provision of silicone-based SGP lenses which are prepared by a process in which the conventional SGP lens material, i.e., a polymerization product of a composition containing polymerizable vinylic siloxane monomer, is formed into the shape of a lens (e.g., by lathe cutting, cast molding, spin casting or the like) and then, instead of being extracted with a physiological saline solution as is conventional, is extracted utilizing a hydrophilic, polar group-containing, organic solvent. After the organic solvent extraction step, the lens is treated to exchange physiological saline solution for organic solvent in the lens.

By proceeding in this manner it is found that a silicone-based SGP lens can be produced having significantly reduced levels (preferably, undetectable levels) of residual siloxane monomer or other low molecular weight derivatives resulting from the polymerization reaction, and which accordingly are nonirritating in use and can be worn for extended periods without deposition problems.

DETAILED DESCRIPTION OF THE INVENTION

For carrying out the present invention, the conventional silicone-based SGP lens materials are employed, as set forth in the earlier-mentioned patents, all of which are incorporated herein by reference.

Thus, the silicone-based SGP lenses known in the art and to which this invention is applicable are formed, for example, from the polymerization product of compositions containing at least one polymerizable vinylic siloxane monomer and at least one hydrophilic vinylic monomer. The polymerizable vinylic siloxane monomer contains at least one polymerizable vinylic group such as an acrylic, styrenyl or vinylic group and at least one polysiloxanyl group. Exemplary polymerizable vinylic siloxane monomers are:

(I): Methyldi(Trimethylsiloxy)Silylpropyl-Glycerol-Ethyl Methacrylate

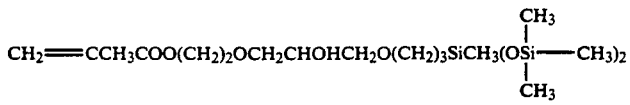

(II): γ-Tris(Trimethylsiloxy)Silylpropyl Methacrylate

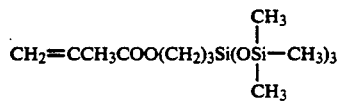

Hydrophilic vinylic monomers suitable for use in SGP lens compositions include N,N-dimethylacrylamide, 2-hydroxyethyl methacrylate, glyceryl methacrylate, and the like.

The compositions and technologies for fabrication of SGP lenses per se, such as lathe cutting, cast molding and spin casting, are well known in the art as exemplified in all the U.S. Patents mentioned previously, all of which are expressly incorporated herein by reference.

In accordance with the invention, the SGP material, in the form of a lens, is thereafter subjected to extraction with a hydrophilic, polar group-containing, organic solvent (hereinafter referred to as PGS). For the SGP lenses formed by co-polymerization of polymerizable vinylic siloxane monomer with hydrophilic vinylic monomer which are conventionally hydrated to a water content of from about 30 to 75 percent by weight to form soft lenses, the PGS extraction is preferably conducted after this initial hydration step.

The PGS for use in the invention can be selected from a wide variety of materials, the particular choice of which will be dictated to varying degrees by availability, cost, and extraction ability for the particular residual components in the particular silicone-containing SGP lens material being employed. Preferably, the selected PGS is an alcohol (ROH), ketone (RCOR'), aldehyde (RCHO), ester (RCOOR'), amide (RCONR'R") or N-alkyl pyrrolidone, where R,R' and R" are the same or different and are alkyl or, if applicable, hydrogen. Most preferably, the alkyl substituents are $C_2$ to $C_5$ alkyls, which may be substituted or unsubstituted, and particularly preferred PGS's are the $C_1$ to $C_5$ alcohols, most particularly isopropanol. The PGS can be mixtures of one or more of these PGS's. Based upon the findings earlier noted regarding the ineffectiveness of 50/50 v/v methanol/water admixtures in extracting silicone-based SGP materials, it is generally preferred that the PGS be employed in complete absence of water. However, for certain PGS's and certain SGP materials, it may be possible to still obtain efficient extraction when the solvent is in admixture with water as a minor component or when the admixture can effectively dissolve all the ingredients of silicone monomers.

The PGS extraction of the SGP lenses of this invention preferably is performed by soaking of the lens in the solvent, preferably with stirring, or alternatively by Soxhlet extraction, for a period of time effective to reduce the residual siloxane monomer or other low molecular weight by-products of the polymerization reaction to acceptably low, preferably undetectable, levels. The completion of the extraction can be monitored by gas chromatography (GC) of the residual irritants, such as residual monomer level, or the under agar cytotoxicity test, i.e., immersion of the extracted lens in agar to test for negative cytotoxicity response. Generally, 20-40 hours of extraction is adequate in an immersion process. If a Soxhlet extraction unit is employed, the extraction period generally can be substantially shortened. When required, a repeated extraction can also be performed. Preferably, the extraction will be conducted at temperatures in the range of from about 20° C. to 60° C.

After the extraction is completed, the PGS inside the lens has to be replaced by a physiological saline solution either by a solvent exchange or by vacuum stripping to dry out the solvent inside the lens, followed by reconditioning the lens in a physiological saline solution. It has been found that after PGS extraction, the SGP lens becomes extraordinarily expanded, the lens parameters become abnormally large, and the strength of the lens becomes extremely weak. In this state the lens can easily be broken into pieces if it is handled and forced such as by a forceps. As a consequence, the use of a PGS extraction would normally be considered quite unacceptable, particularly since the weak strength logically could be attributed to the irreversible breaking of the material bonds by the mechanical expansion. However, it has been found that use of a gentle handling process after the extraction is completed, i.e., so as not to apply a mechanical force to the lens as can occur using a forceps to handle the lens or to transfer the lens after the PGS inside the lens is replaced by a physiological saline solution, the lens strength and the lens parameters can surprisingly be restored.

The lenses thus made do not contain any detectable residual irritants or residual silicone monomer and show no cytotoxicity response. Clinically, the lenses thus made do not show any irritation to the eye. The lenses are extremely comfortable and can be worn for a long period of time without deposition problem.

Although not wishing to be bound by any theory as such, it is postulated that the substantially improved comfort and wearability of the lenses made from this invention result from the fact that the residual siloxane monomers and/or derivatives formed during the polymerization reactions are essentially extracted out of the lenses thereby precluding the problem with conventionally-prepared SGP lenses where these residuals leach out to the lens surface in use and have a detrimental effect on the lens wettability, comfort and thus deposition problem and lens wearability.

The present invention is further illustrated and described with reference to the following example.

EXAMPLE

SGP lenses were fabricated from buttons which were made according to the formulations and procedures set forth in U.S. Pat. No. 4,182,822, the starting formulation consisting of 36% by weight γ-tris(trimethylsiloxy) silylpropyl methacrylate (prepared according to Example 1 of the above patent), 44% by weight N,N-dimethylacrylamide (NNDMA, a hydrophilic monomer) and 20% by weight 2-hydroxyethylmethacrylate (HEMA), with 0.3% by weight t-butyl peroxypyvalate included as a catalyst. The formulation was placed in a Teflon tube. After deoxygenation by nitrogen for fifteen minutes, the tube was sealed and the formulation was polymerized in a 40° C. water bath for six (6) hours, followed by a 100° C. treatment for another six hours. The buttons cut from the rods were post-cured at 110° C. under high vacuum (0.5 Torr) for 44 hours. Alternatively, the lenses could also be made from the formulation by cast molding or spin casting, techniques which are well known in the art.

After hydration, the lenses were subjected to the conventional approach of extraction in a physiological saline solution, at 60° C. for 6 hours as practiced in the manufacture of the conventional soft lenses. Generally, the residual silicone monomers level in these extracted lenses monitored by GC was about 0.2%–0.5% by weight, and the level of hydrophilic monomer was about 0.02–0.4% by weight. The lenses showed cytotoxicity response in agar testing. In clinical evaluation, lenses of this type were very irritable, uncomfortable and highly clinically unacceptable.

However, in a separate experiment, the lenses after hydration were separately soaked in 4 ml isopropanol, a hydrophilic, polar group-containing, solvent, for 18 hours, followed by re-soaking in another 4 ml fresh isopropanol for 6 hours. Then isopropanol was decanted and replaced by a physiological saline solution without applying mechanical force to the lenses. The lenses thus prepared contained no detectable residual monomer by GC and showed no cytotoxic response in agar test. In clinical evaluation, the lenses showed no irritation and were very comfortable in extended wear.

The strength of the lenses was also surprisingly recovered after extraction.

In alternative methods, the SGP lens materials of this Example can be extracted under similar conditions using for example, acetone, methyethyl ketone, methyl acetate, N,N-dimethylacetamide or N-methyl pyrrolidone.

Although the invention has been described in connection with particular preferred embodiments, it is not intended to limit the invention to particular forms set forth, but on the contrary, it is intended to cover such alternatives, modifications and equivalents as may be included within the spirit and scope of the invention as defined by the appended claims.

What is claimed is:

1. In a process for producing a silicone-based hydrophilic soft gas permeable contact lens containing at least about 30% water by weight, wherein a lens material comprising the polymerization product of a composition comprising γ-tris (trimethylsiloxy)silylpropyl methacrylate, N,N-dimethylacrylamide and 2-hydroxyethylmethacrylate, is formed in the shape of a contact lens, followed by subjecting of the contact lens to extraction with water or physiological saline solution, the improvement comprising conducting the extraction of said contact lens using an alcohol of the formula ROH, where R is alkyl, and thereafter subjecting the so-treated lens to treatment with a physiological saline solution to exchange said solution for said alcohol in the lens, so as to produce a contact lens which is essentially free of extractable residual siloxane monomer.

2. A process according to claim 1 wherein R is a $C_1$ to $C_5$ alkyl.

3. A process according to claim 2 wherein said alcohol is isopropanol.

* * * * *